(12) United States Patent
Viskov et al.

(10) Patent No.: US 7,687,274 B2
(45) Date of Patent: Mar. 30, 2010

(54) METHOD FOR DETERMINING SPECIFIC GROUPS CONSTITUTING HEPARINS OR LOW MOLECULAR WEIGHT HEPARINS

(75) Inventors: Christian Viskov, Ris Orangis (FR); Pierre Mourier, Charenton le Pont (FR)

(73) Assignee: Aventis Pharma S.A., Paris (FR)

( * ) Notice: Subject to any disclaimer, the term of this patent is extended or adjusted under 35 U.S.C. 154(b) by 0 days.

(21) Appl. No.: 12/007,695

(22) Filed: Jan. 14, 2008

(65) Prior Publication Data

US 2009/0023171 A1  Jan. 22, 2009

Related U.S. Application Data

(63) Continuation of application No. 10/808,410, filed on Mar. 25, 2004, now abandoned.

(30) Foreign Application Priority Data

Feb. 24, 2004 (FR) .................................. 04 01810
Mar. 24, 2004 (EP) .................................. 04290789

(51) Int. Cl.
*C12Q 1/34* (2006.01)
*G01N 30/02* (2006.01)

(52) U.S. Cl. .............................. 436/94; 435/4; 435/18; 73/61.52

(58) Field of Classification Search ....................... None
See application file for complete search history.

(56) References Cited

U.S. PATENT DOCUMENTS

| | | | | |
|---|---|---|---|---|
| 4,981,955 A | * | 1/1991 | Lopez | 536/21 |
| 5,039,529 A | * | 8/1991 | Bergendal et al. | 424/63 |
| 5,389,618 A | * | 2/1995 | Debrie | 514/56 |
| 5,569,600 A | * | 10/1996 | Sasisekharan et al. | 435/220 |
| 6,617,316 B1 | * | 9/2003 | Mourier et al. | 514/56 |

* cited by examiner

*Primary Examiner*—Krishnan S Menon
*Assistant Examiner*—Rebecca Fritchman
(74) *Attorney, Agent, or Firm*—Finnegan Henderson Farabow Garrett & Dunner LLP

(57) ABSTRACT

The invention provides methods for analyzing heparins, low-molecular-weight heparins, ultralow-molecular-weight heparins, and oligosaccharides by high performance liquid chromatography a stationary phase dynamically coated with a quaternary ammonium salt. The methods of the invention may be used to analyze samples without pre-treatment or to analyze samples that have been partially or exhaustively depolymerised and, optionally, reduced. Specific saccharides can be detected.

25 Claims, 7 Drawing Sheets

Figure 5a and b:

METHOD FOR DETERMINING SPECIFIC GROUPS CONSTITUTING HEPARINS OR LOW MOLECULAR WEIGHT HEPARINS

This application is a continuation of U.S. application Ser. No. 10/808,410, filed Mar. 25, 2004 now abandoned and claims the benefit of French Patent Application No. 0401810, filed Feb. 24, 2004, and European Patent Application No. 04 290789.9, filed Mar. 24, 2004. The entire disclosures of each of these applications are hereby incorporated herein by reference for all purposes.

The present invention provides methods for the direct analysis of oligosaccharides constituting heparins low-molecular-weight heparins (LMWH), or ultralow-molecular weight heparins (ULMWH).

Heparins are biologically active agents of the glycosaminoglycan family, extracted from natural sources, and have valuable anticoagulant and antithrombotic properties. In particular, they are useful in the treatment of postoperative venous thromboses.

To create LMWH from source heparin, the longer heparinic polysaccharide chains are broken down into shorter chains of lower molecular weight. This is done by either chemical or enzymatic depolymerization. For example in the case of enoxaparin, the depolymerization process involves two competing chemical reactions, namely β-elimination and hydrolysis of the benzyl esters. The result is average molecular weights for LMWH polysaccharide chains of approximately 4500 Da. LMWHs, like unfractionated heparin, inhibit coagulation by binding to ATIII at particular pentasaccharide sequences distributed along some of the polysaccharide chains.

Each LMWH manufacturer of an approved product utilizes a distinct process of depolymerization. Unless two manufacturers use the same process, this process distinctness results in LMWHs with distinct chemical structures and, therefore, differing pharmacological activity and different approved indications for clinical use.

Therefore, LMWHs are structurally differentiated by the depolymerization processes used for their manufacture (R. J. Linhardt, et al, Seminars in Thrombosis and Hemostatis 1999; 25(3 Supp.): 5-16). As a result, LMWHs are more heterogeneous than heparin. Each different process causes unique and highly complex structural modifications to the polysaccharide chains. These modifications include differences in chain lengths and chain sequences, as well as structural fingerprints. Consequently, the different LMWHs each have distinctive pharmacological profiles and different approved clinical indications.

During the process for preparing enoxaparin sodium, sold under the tradename Lovenox® in the US and Clexane® in some other countries, from pure heparin, the aqueous-phase alkaline depolymerization process produces a partial but characteristic conversion of the glucosamines of the reducing ends of the oligosaccharide chains.

The first step of this conversion consists of a glucosamine ↔ mannosamine epimerization (T. Toida, et al., J. Carbohydrate Chemistry, 15(3), 351-360 (1996)); the second step is a 6-O-desulfation of the glucosamine, leading to the formation of derivatives called "1,6 anhydro" (International patent application WO 01/29055).

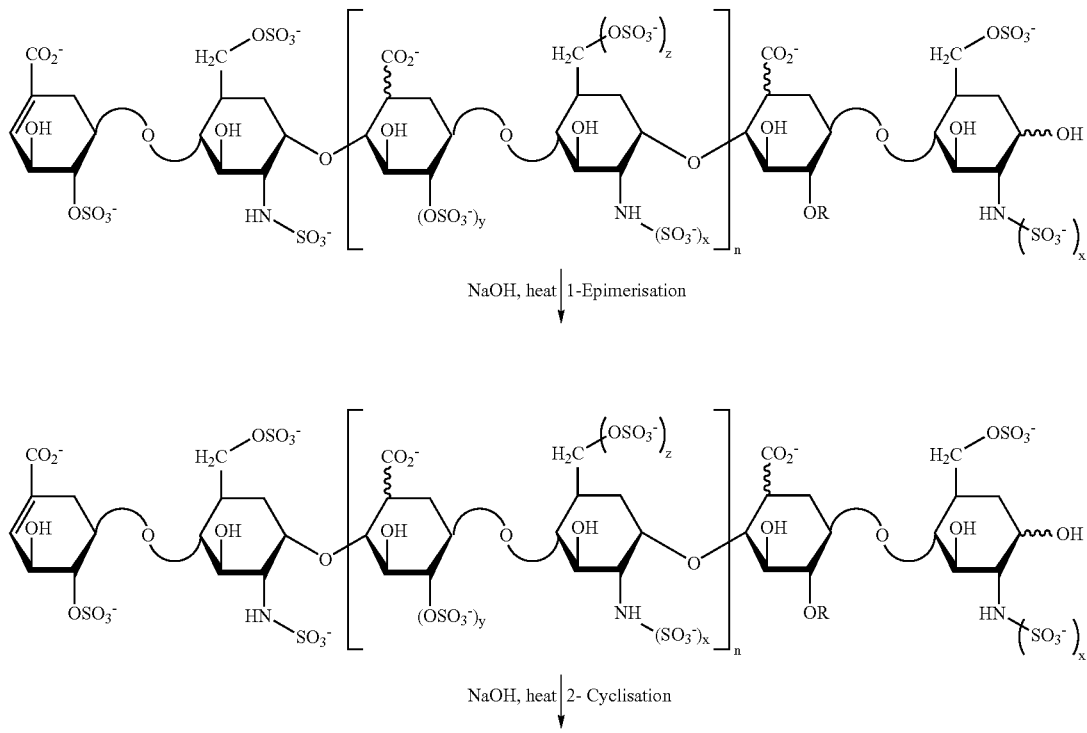

-continued

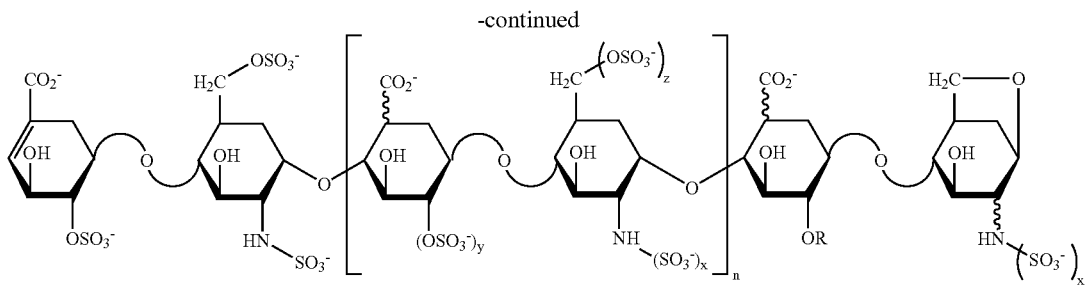

This type of derivative is obtained for oligosaccharide chains whose terminal glucosamine is 6-O-sulfated.

The percentage of oligosaccharide chains whose end is modified with a 1,6-anhydro bond is a structural characteristic of the oligosaccharide mixture of Lovenox® (enoxaparin sodium). Based on current knowledge, between 15% and 25% of the components of Lovenox® (enoxaparin sodium) have a 1,6-anhydro structure at the reducing end of their chain.

Recently, new processes for the preparation of heparin fragments employing depolymerization in the presence of a strong base have yielded ultra-low molecular weight heparins having a weight average molecular weight ranging from approximately 1500 to approximately 3000 Daltons (ULM-WHs) as described, e.g., in U.S. Published Patent Application No. 2002-0055621 A1, specifically incorporated by reference herein.

Analysis of heparin, low-molecular weight heparin, or ultralow-molecular weight heparin either as intact molecules or as enzymatic digests is a difficult task due to the polydispersity of the mixtures as well as the high and variable degree of functionalisation of the molecules. Chromatographic and electrophoretic methods were developed in order to address this issue. Capillary electrophoresis (CE) is used for the separation of heparin oligosaccharides (M. Guerrini, et al., Glycobiology 12 (2002) 713-719; R. J. Linhardt., et al., BioMethods (Basel) 9 (1997)183-197). However, the selectivity of CE is rather poor compared to liquid chromatography. Moreover, detection in CE (by UV) is often a problem due to insufficient sensitivity. An additional drawback of CE is the inability to adapt separations developed for this analytical method to preparative techniques.

In some cases, MALDI-TOF mass spectrometric analysis can be performed without chromatographic separations and may be used as a preliminary method for the analysis of heparin oligosaccharides and as a sequencing tool (H. Sakaguchi et al., J. Biochem. 129(2001)107-18; A. J. Rhomberg, et al., Proc. Natl. Acad. Sci. USA 95 (1998)4176-4181; L. Sturiale, et al., Semin. Thromb. Hemost. 27 (2001)465-472). However, MALDI-TOF mass spectrometric analysis cannot resolve complex mixtures and is expensive.

For these reasons, liquid chromatography is preferred for the separation of sulfated oligosaccharides. Strong anion exchange (SAX) with sodium chloride based mobile phases is one chromatographic method for resolving heparin-derived oligosaccharides. In addition, gel permeation chromatography by HPLC or by low-pressure chromatography is a powerful tool for the size separation of oligosaccharides and for desalting applications.

The use of sodium chloride in the mobile phase for these methods can have two serious drawbacks: mobile phases comprising NaCl require a chromatograph specially treated to overcome the corrosive effects of the salt and have a strong UV absorbance at wavelengths below 215 nm, which limits the use of certain methods for detecting oligosaccharides.

For this reason, the development of stationary phases for SAX chromatography has been limited. Often, the use of SAX chromatography is limited to the separation of oligosaccharides containing less than 5-10 sulfates, with frequently significant peak broadening for highly sulfated products as a consequence of poor mass transfer into the pores of the stationary phase. The alternative of ion-pair chromatography on $C_{18}$ or $C_8$ bonded silica with mobile phases containing tetra butyl ammonium (N. K. Karamanos et al., J. Chromatogr. 765 (1997) 169-179; C. F. Moffat, et al., Eur. J. Biochem., 197 (1991) 449-459) or the equivalent is also limited to low sulfated species because of the decrease of selectivity observed at the end of the acetonitrile elution gradient. An interesting development of ion pair chromatography has recently been reported by Linhardt et al. (J. Chromatogr., 1014 (2003) 215-223). Although this method may be easily coupled with mass spectroscopy, its use also is limited by the selectivity for highly sulfated oligosaccharides. Ion pairing with more lipophilic ammonium salts such as cetyl trimethyl ammonium (CTA) is difficult because they form very apolar ion-pairs with sulfated oligosaccharides, most of which are insoluble in aqueous solvents.

Some separations of mineral anions using stationary phases previously adsorbed by an ion-pairing agent such as CTA have been performed by Ito, et al. (J. Chromatogr., 549 (1991) 265-272; Anal. Chem., 63 (1991) 273-276.; J. Chromatogr., 598 (1992) 237-241).

Therefore, an aspect of the invention is to provide new methods of sequencing that allow the separation and analysis of highly charged oligosaccharides as large as dodecasaccharides and with up to 20 sulfate groups.

A further aspect of the invention provides a method of assaying a sample chosen from heparin, low-molecular-weight heparin, ultra low molecular weight heparin, and oligosaccharides, wherein the sample is analyzed using a reversed phase column coated with a quaternary ammonium salt for chromatographic separation and analysis of a complex mixture of oligosaccharides. In a related aspect of the invention, the reversed phase column is a $C_8$ or $C_{18}$ column.

In one embodiment, the method of the invention employs analytical high performance liquid chromatography using a stationary phase prepared by dynamically coating a $C_8$ or $C_{18}$ reversed phase column with quaternary ammonium salt solutions. (It is understood that the reversed phase is not limited to $C_8$ or $C_{18}$ and other reversed phases may be suitable for this purpose.)

In an embodiment of the invention, the stationary phase is a $C_8$ or $C_{18}$ reversed phase column dynamically coated with a cetyl trimethyl ammonium salt or cetyl pyridinium salt). The reversed phase column may be, for example, Hypersil BDS In the present invention, the phrase "heparin" means all forms of heparin other than a heparin product, including without limitation crude heparin, upgraded heparin and purified heparin. In the present invention, the phrase "heparin product" means LMWHs and ULMWHs In the present invention, the phrase "low molecular weight heparin" or "LMWH" means a mixture of polysaccharides obtained from heparin and having a weight average molecular weight greater than approximately 3,000 Daltons and less than approximately 10,000 Daltons.

In the present invention, the phrase "ultra-low molecular weight heparin" or "ULMWH" means a mixture of polysaccharides obtained from heparin having a weight average molecular weight ranging from approximately 1500 to approximately 3000 Daltons.

As used herein, CTA-SAX chromatography refers to anion exchange chromatography conducted on a quaternary ammonium salt dynamically coated on a reversed phase silica column that maintains a constant net positive charge in the range of about pH 2 to about pH 12.

In one embodiment of the invention, the reversed phase column may be an octyl or an octadecyl silica column.

In one embodiment of the invention, the quaternary ammonium salt may be cetyl trimethyl ammonium or cetyl pyridinum.

In an embodiment of the invention, CTA-SAX chromatography uses a solid support comprising an octyl or an octadecyl bonded silica coated with cetyl trimethyl ammonium or cetyl pyridinum. In this embodiment, conventional octyl or octadecyl bonded silica are "dynamically coated" by cetyl trimethyl ammonium (CTA) or cetyl pyridinum salt solutions, and their anionic exchange capacity is carefully controlled by the quantity of adsorbed CTA or cetyl pyridinum.

In one embodiment, the stationary phase for chromatography is a cetyl trimethyl ammonium salt-coated Hypersil BDS $C_8$ or $C_{18}$ reversed phase column.

The methods of analysis according to the invention include the following:

Direct analysis can be performed by high performance liquid chromatography using a stationary phase prepared by dynamically coating a $C_8$ or $C_{18}$ reversed phase column with quaternary ammonium salt solutions (e.g., CTA-SAX chromatography) of the sample and detection of all of the oligosaccharides from disaccharides to dodecasaccharides. In this case, the oligosaccharide sequences are observed as they are in the product. This is an analysis that allows the direct examination of the oligosaccharides.

Combined analysis by gel permeation chromatography (GPC of the sample to be analysed) and by high performance liquid chromatography using a stationary phase prepared by dynamically coating a $C_8$ or $C_{18}$ reversed phase column with quaternary ammonium salt solutions (e.g., CTA-SAX chromatography) also may be used to analyze oligosaccharides from di to dodecasaccharides. This two-dimensional separation methodology increases the resolving power and allows a direct examination of the oligosaccharides in the sample. In addition, the two-dimensional analysis minimizes the possibility that oligosaccharide peaks will overlap. This too is a method that allows direct observation of the oligosaccharides as they are in the sample tested.

The sample to be assayed may also be depolymerized before analysis by high performance liquid chromatography using a stationary phase prepared by dynamically coating a $C_8$ or $C_{18}$ reversed phase column with quaternary ammonium salt solutions (e.g., CTA-SAX chromatography). In this embodiment of the invention, the sample may be depolymerized either partially or totally by the action of heparinases and then, where appropriate, the depolymerizate obtained may be reduced. The depolymerizate may then be analyzed, for example, by CTA-SAX chromatography or a combination of gel permeation and CTA-SAX chromatography.

In a specific embodiment, the depolymerizate is reduced by treatment with $NaBH_4$ and then analysed by CTA-SAX chromatography or a combination of gel permeation and CTA-SAX chromatography.

In one embodiment, the method according to the invention may be used to analyse heparins, low-molecular-weight heparins (LMWH), ultra low molecular weight heparins (ULMWH), and oligosaccharides directly by using a quaternary ammonium salt coating of $C_8$ or $C_{18}$ reversed phase column for separating and analyzing complex mixtures of oligosaccharides with all of the oligosaccharides from disaccharides to dodecasaccharides detected.

In a related embodiment, the analysis is carried out by CTA-SAX chromatography.

In another embodiment, the method of analysing heparins, low-molecular-weight heparins, ultra low molecular weight heparins and oligosaccharides involves two steps a) a first separation by gel permeation chromatography and then b) a second separation of each fraction from di to dodecasaccharides using a quaternary ammonium salt coating of $C_8$ or $C_{18}$ reversed phase column for separation with a detection of all the oligosaccharides from disaccharides to dodecasaccharides.

In a related embodiment, the above-mentioned analysis the second separation is carried out by CTA-SAX chromatography.

In another embodiment of the invention, the method of analysing heparins, low-molecular-weight heparins, ultra low molecular weight heparins, and oligosaccharides includes a step in which the sample is depolymerized either partially or totally, for example, by the action of heparinases and then, where appropriate, the depolymerizate is reduced. Analysis is then directly carried out by using a quaternary ammonium salt coating of $C_8$ or $C_{18}$ reversed phase column for separation and analysis of complex mixture of oligosaccharides with a detection of all the oligosaccharides from disaccharides to dodecasaccharides In a related embodiment, the above mentioned analysis is carried out by CTA-SAX chromatography.

The methods of the invention may be used to determine the selectivity of the depolymerization process used to prepare LMWH, ULMWH, and oligosaccharides. The ability to directly analyse oligosaccharides up to dodecasaccharides allows one to determine what oliogosaccharide sequences are generated by a particular depolymerization process. As noted previously, unless at least two manufacturers are utilizing an identical process, each LMWH manufacturer utilizes a distinct process of depolymerization, resulting in LMWHs with distinct chemical structures and, therefore, differing pharmacological activity and different approved indications for clinical use. The methods of the invention now provide a way to identify and characterize the unique highly complex structural profile of each LMWH or ULMWH.

The methods of the invention may also be used to detect and/or quantify the presence of oligosaccharide chains whose end is modified with a 1,6-anhydro bond ("1,6-anhydro groups") or any other particular structural modification generated by the manufacturing process.

In one embodiment of the invention, the sample to be assayed may be directly analysed and/or quantified (i.e., without enzymatic or chemical pre-treatment) for the presence of "1,6-anhydro groups" by CTA-SAX chromatography up to dodecasaccharides.

In another embodiment of the invention, "1,6-anhydro groups" may be directly analysed and/or quantified in a sample by fractionation of the sample using gel permeation chromatography followed by CTA-SAX chromatography of each fraction from di to dodecasaccharides. The methods of the invention permit one to identify distinct oligosaccharides bearing the 1,6 anhydro groups and their distribution in this part of the sample (di to dodecasaccharide).

In another embodiment of the invention, "1,6-anhydro groups" are analysed in a sample that has been exhaustively depolymerized with a mixture of heparinases.

In a related embodiment, the mixture of heparinases comprises heparinase 1 (EC 4.2.2.7.), heparinase 2 (heparin lyase II), and heparinase 3 (EC 4.2.2.8.), for example with each heparinase being present as 0.5 units/ml. (These enzymes are marketed by the group Grampian Enzymes).

The methods according to the invention allow the differentiation of Lovenox® (enoxaparin sodium) from low-molecular-weight heparins that do not contain "1,6-anhydro" derivatives. Conversely, the methods according to the invention make it possible to ascertain that low-molecular-weight heparins do not have the physicochemical characteristics of Lovenox® (enoxaparin sodium).

In addition, the methods of the invention may be applied to industrial processes during in-process control of samples in order to provide standardization of the process for manufacturing LMWH and ULMWH by chemical or enzymatic depolymerization involving β-elimination, including Lovenox® (enoxaparin sodium), and to obtain uniform batches.

In one embodiment, the methods of the invention may be used to characterize Lovenox® (enoxaparin sodium) by:

depolymerizing a sample of Lovenox® (enoxaparin sodium) with a mixture of heparinase 1 (EC 4.2.2.7.), heparinase 2 (heparin lyase II), and heparinase 3 (EC 4.2.2.8.);

optionally, reducing the depolymerized sample, for example, by treatment with a $NaBH_4$ solution in sodium acetate. (This step makes it possible to specifically reduce the reducing ends which are not in the 1,6-anhydro form (products described in patent application WO 01/72762)); and separating the various oligosaccharides in the depolymerized and optionally reduced sample by HPLC (High Performance Liquid Chromatography).

In one embodiment of the invention, the HPLC may be CTA-SAX chromatography (as defined above).

In another embodiment, the invention provides a method for preparing an HPLC stationary phase comprising dynamically coating a $C_8$ or $C_{18}$ reversed phase column with a quaternary ammonium salt to be utilized, for example, in a method of analysing heparins, low-molecular-weight heparins, ultra low molecular weight heparins, and oligosaccharides, as described herein. In a specific embodiment, the quaternary ammonium salt is cetyl trimethyl ammonium hydrogensulfate and the dynamic coating is performed in a $H_2O$—$CH_3OH$ solution at a column temperature of about 45° C. The amount of CTA adsorbed on the column is directly related to the methanol percentage contained in the percolated solution and can be modulated accordingly.

In the CTA-SAX chromatography utilized in the present invention, the $C_8$ or $C_{18}$ reversed phase column may be, for example, Hypersil BDS columns or Hypersil P basic (Thermo Finnigan). For analytical work, the $C_8$ or $C_{18}$ reversed phase column may have a particle size of 3 µm, a column length of about 15 cm, and a column diameter of between about 1 mm and about 4.6 mm. For preparative purposes, the $C_8$ or $C_{18}$ reversed phase column may have a larger diameter, for example, 50 mm and a larger particle size, for example, 8 µm.

One skilled in the art, by varying the amount of CTA absorbed on the column, the particle size, the column diameter, and the column length, can separate highly charged oligosaccharides as large as dodecasaccharides and with up to 20 sulfate groups. Moreover, the recent development of octadecyl-bonded silica permits the use of 3 µm particles with high efficiency.

In the methods according to the present invention, the retention time of sulfated oligosaccharides is directly adjustable depending on the amount of cetyl trimethyl ammonium salt adsorbed into the column. Oligosaccharides containing up to 20 sulfates may be separated with a resolving power superior to that of conventional SAX analysis. The stability of the column coating enables hundreds of injections.

The invention also provides a simplified method of oligosaccharide sequencing based on the partial depolymerization by lyases of heparin, LMWH, or ULMWH. Moreover, the CTA-SAX methods of the invention are directly transposable to preparative scale operations as mentioned above.

Desorption of CTA from the column is possible if organic solvents such as methanol or acetonitrile, pure or mixed with water, are passed through the column. However as long as aqueous mobile phases are used, CTA remains adsorbed on the column, and the column may be used for at least several months. During that time, the column retention remains relatively stable, although a small decrease in retention may be observed, especially in the initial period of use (K. Ito et al., J. Chromatogr., 549 (1991) 265-272A)

An additional property of the CTA-SAX columns of the invention is their capacity to resolve the α and β anomers at the oligosaccharide reducing end. The molar ratio between the two anomers depends on the sulfation pattern of the reducing terminal. With a N-sulfated glucosamine at the reducing end, the ratio anomer α/anomer β is about 95/5, whereas with a N-acetylated glucosamine, this ratio ranges from 60/40 to 40/60. Similarly, sulfation at positions 6 and 3 on the glucosamine gives characteristic elution patterns for the anomers. A very specific anomeric pattern is also observed on oligosaccharides ending with a mannosamine (such as ΔIs-$Is_{id}^{epi}$). As previously mentioned, this special structure is characteristic of Lovenox® (enoxaparin sodium) and is generated by the epimerisation of the reducing end in alkaline media during the chemical process.

The equipment used may be any chromatograph that allows the formation of an elution gradient and that is equipped with a UV detector. In one embodiment of the invention, the UV detector is an array of diodes that permits the generation of UV spectra of the constituents and allows complex signals resulting from the difference between the absorbance at 2 different wavelengths to be recorded. Such a diode array detector facilitates the specific detection of acetylated oligosaccharides. In a related embodiment, HPLC mobile phases that are transparent in the UV region from about 200 nm to about 400 nm are used. Mobile phases that can be used according to this embodiment of the invention include, but are not limited to mobile phases based on sodium perchlorate or methanesulfonate salts. In one embodiment, the mobile phase is an aqueous solution of ammonium methane sulfonate.

A subject of the invention is therefore also a method of analysis as defined above by separation by anion-exchange chromatography, wherein a mobile phase that is transparent in the UV region from about 200 nm to about 400 nm is used.

In certain embodiments, the strong anion chromatography separation is performed at a pH from about 2.0 to about 7.0.

Higher pH conditions can also be used. In a related embodiment, a pH of about 2.5 will be used. In another embodiment, the developing ion is ammonium methane sulfonate, which may be prepared by neutralization of methane sulfonic acid to pH 2.5 by ammoniac aqueous solutions.

Exemplary chromatographic separation conditions are given below:

Solvent A: Milli-Q quality water brought to pH 3 by the addition of methane sulfonic acid Solvent B: 2M ammonium methane sulfonate at pH 2.5

The linear elution gradient may be the following:

T=0 min: % B=1; T=74 min: % B=100

Flow rate: 0.22 ml/mn, Column temperature 40° C.

A further aspect of the invention is a method of detecting specific groups found in heparins or low-molecular-weight heparins (LMWH) or Ultra low-molecular-weight heparins.

In one embodiment, this method increases the specificity of the UV detection of heparin or LMWH groups. As nonacetylated polysaccharides all have, at a given pH, a fairly similar UV spectrum, it is possible to selectively detect the acetylated sugars by taking as signal the difference between the absorbance at 2 wavelengths chosen such that the absorptivity of the nonacetylated saccharides cancels out.

As illustrated below by way of example, 202 nm and 230 nm may be chosen as detection and reference wavelengths and the 202-230 nm signal may be recorded. A person skilled in the art will appreciate that the choice of wavelength that can be used will depend on the pH of the mobile phase (adjustments of a few nm may be necessary so as to be at the optimum of said conditions).

Any UV detector that can simultaneously measure absorbance at two or more wavelengths may be used. In one embodiment of the invention, the DAD 1100 detector from the company Agilent Technologies is used. In this embodiment, a double detection will be carried out at 234 nm, on the one hand, and at 202-230 nm, on the other hand. The principle of selective detection of acetylated oligosaccharides is illustrated in FIG. 1 in which the UV spectrum of a sulfated disaccharide ΔIs is compared with that of an acetylated disaccharide ΔIa.

A subject of the present invention is therefore also a method of analysis, wherein the method of detection makes it possible to selectively detect acetylated sugars.

In certain embodiments, the method of analysis uses separation by CTA-SAX chromatography, and acetylated sugars are selectively detected by measuring the difference between the absorbance at 2 wavelengths chosen such that the absorptivity of the nonacetylated saccharides cancels out. Moreover, the methods of the invention allow the quantification of the 4 1,6-anhydro residues described below, which requires a sufficient selectivity of the chromatographic system in relation to all the other constituents of the mixture.

The causes of splitting of the peaks are the anomeric forms, on the one hand, and to a lesser degree the glucosamine ↔ mannosamine epimerisation, which is partially present for ΔIIs, ΔIIIs and ΔIs when they are in the terminal position in the oligosaccharide chain. However, the resolving power of the CTA-SAX method is sufficient to assay all the oligosaccharides in the chromatogram.

After enzymatic depolymerization and reduction of the reducing ends, the 1,6-anhydro derivatives of Lovenox® (enoxaparin sodium) exist in 4 essential forms:

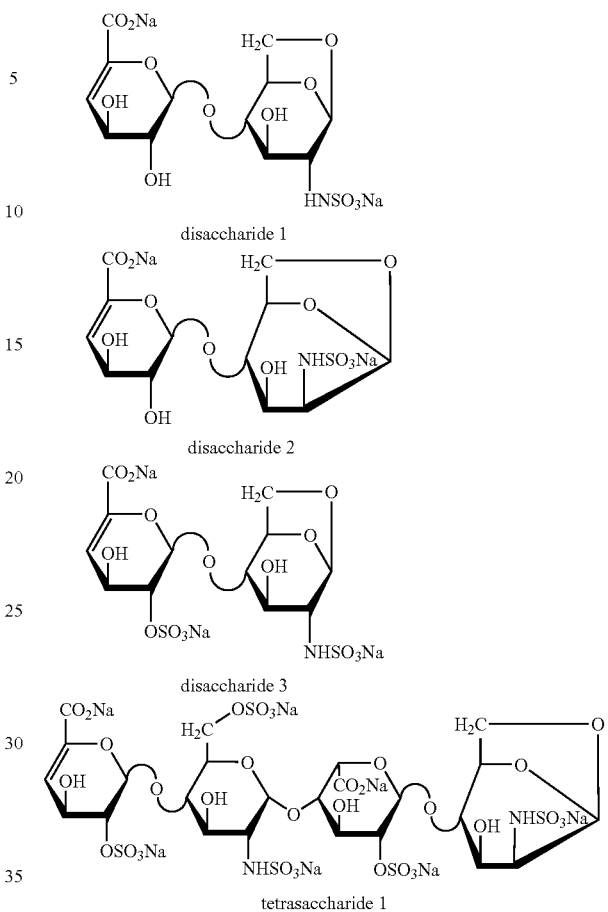

disaccharide 1 disaccharide 2 disaccharide 3 tetrasaccharide 1

All the oligosaccharides or polysaccharides that contain the 1,6-anhydro end on the terminal disaccharide unit and that do not possess a 2-O-sulfate on the uronic acid of said terminal disaccharide are completely depolymerized by the heparinases and are in the form of the disaccharides 1 and 2. On the other hand, when the terminal saccharide contains a 2-O-sulfate on the uronic acid and when it is in the mannosamine form, the 1,6-anhydro derivative is in the form of the tetrasaccharide 1 (form resistant to heparinases).

Trisaccharide 1 (see below) may also be present in the mixture. It is derived from another degradation process that leads to the structure below (peeling phenomenon observed during the chemical depolymerization of Lovenox® (enoxaparin sodium)).

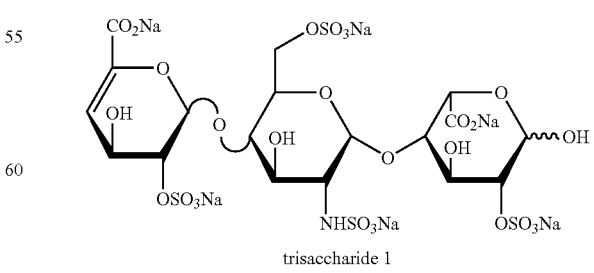

trisaccharide 1

The other constituents of the mixture are not characteristic solely of Lovenox® (enoxaparin sodium). There are of course the 8 elementary disaccharides of the heparin chain. These 8 elementary disaccharides are marketed by the company Sigma and other companies.

Other disaccharides were identified in the mixture by a method according to the invention: the disaccharides $\Delta IIS_{gal}$ and $\Delta IVS_{gal}$, which have as their origin alkaline 2-O-desulfation of -IdoA(2S)-GlcNS(6S)- and of -IdoA(2S)-GlcNS-, leading to the formation of 2 galacturonic acids. They are not usually present in the original structure of heparin (U. M. Desai, et al., Arch. Biochem. Biophys., 306 (2) 461-468 (1993).

ΔIVa
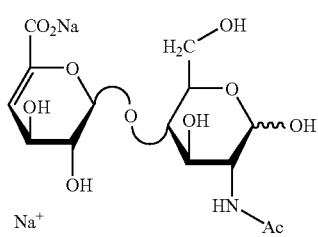

ΔIVs
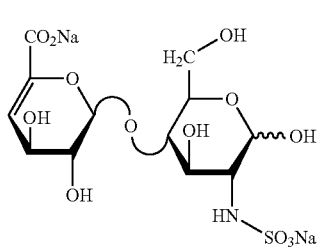

ΔIVs_gal
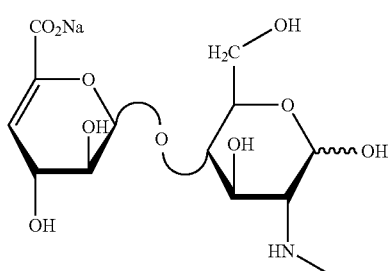

ΔIIa
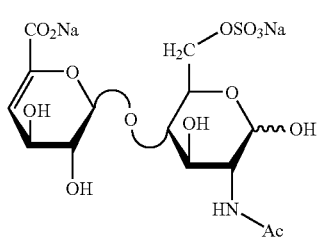

ΔIIs
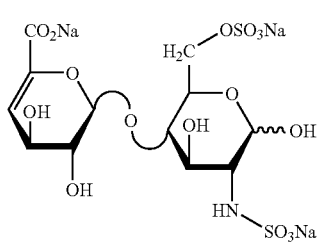

-continued

ΔIIs_gal
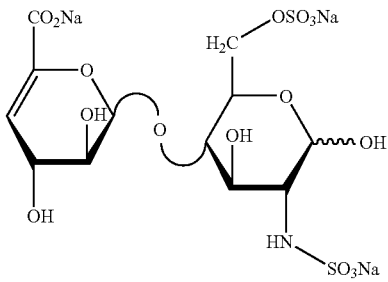

ΔIIIa
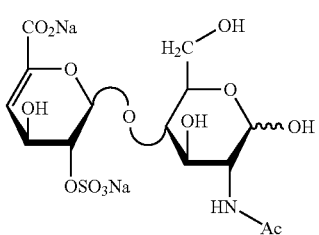

ΔIIIs
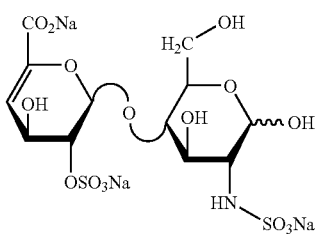

ΔIa
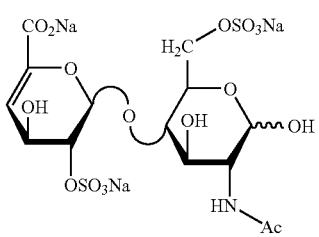

ΔIs
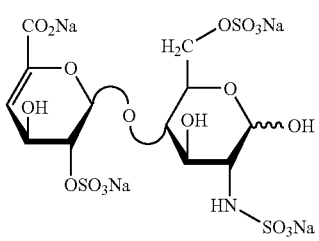

Oligosaccharides containing 3-O-sulfated glucosamines withstand cleavage by heparinases and remain in the form of tetrasaccharides.

In the case of most low-molecular-weight heparins, the heparin is extracted from pig mucosa, and the principal tetrasaccharides are represented below. These tetrasaccharides are resistant to enzymatic depolymerization and comprise the sequences with affinity for antithrombin III. These tetrasaccharides are symbolized as follows: $\Delta IIa\text{-}IIs_{glu}$ and $\Delta IIa\text{-}IVs_{glu}$. (S. Yamada, et al., J. Biol. Chem.; 270(7), 4780-4787 (1993)

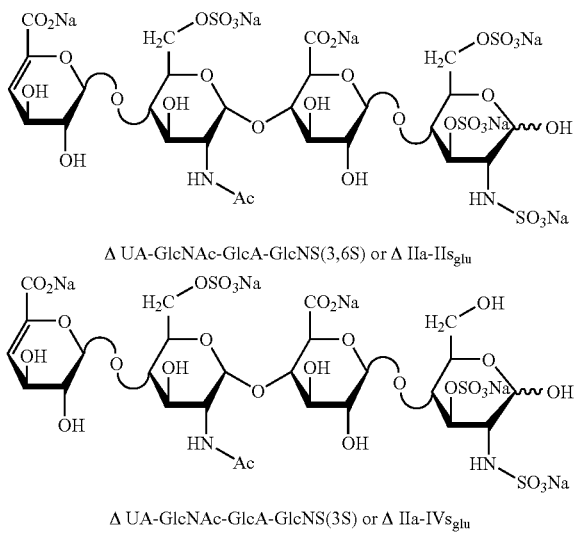

ΔUA-GlcNAc-GlcA-GlcNS(3,6S) or Δ IIa-IIs$_{glu}$

ΔUA-GlcNAc-GlcA-GlcNS(3S) or Δ IIa-IVs$_{glu}$

The final constituent of the mixture cleaved with heparinases is the glycoserine end ΔGlcA-Gal-Gal-Xyl-Ser (K. Sugahara, et al., J. Biol. Chem.; 270(39), 22914-22923 (1995); K. Sugahara,; J. Biol. Chem.; 267(3), 1528-1533 (1992)).

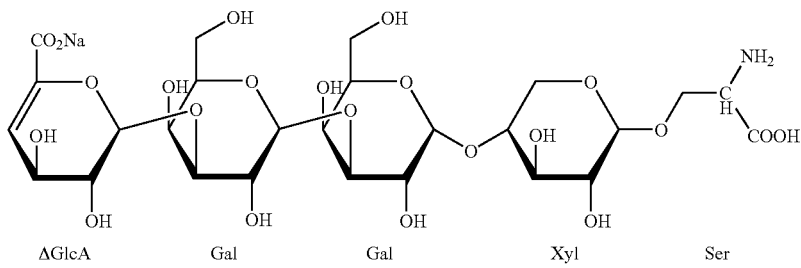

According to one embodiment of the invention, a GPC column is directly coupled to a CTA-SAX column in order to obtain a two dimensional profile of analyzed oligosaccharide mixtures. In a related embodiment, a method for sequencing heparin oligosaccharides resulting from the partial depolymerization of a sample by heparinases according to their size and sulfation pattern and digest analysis by CTA-SAX may be performed using an analytical GPC column directly coupled to a CTA-SAX column in order to obtain a two dimensional profile of analyzed oligosaccharide mixtures.

BRIEF DESCRIPTION OF THE DRAWINGS

Of course, the methods of the invention for analysing heparins, low-molecular-weight heparins including, but not limited to, Lovenox® (enoxaparin sodium), ultra low molecular weight heparins, and oligosaccharides (up to dodecasaccharides) may be applied to any LMWH seeking approval by a regulatory authority pursuant to an application citing Lovenox®/Clexane® (enoxaparin sodium injection) as the listed drug.

EXAMPLES

Figure 1:
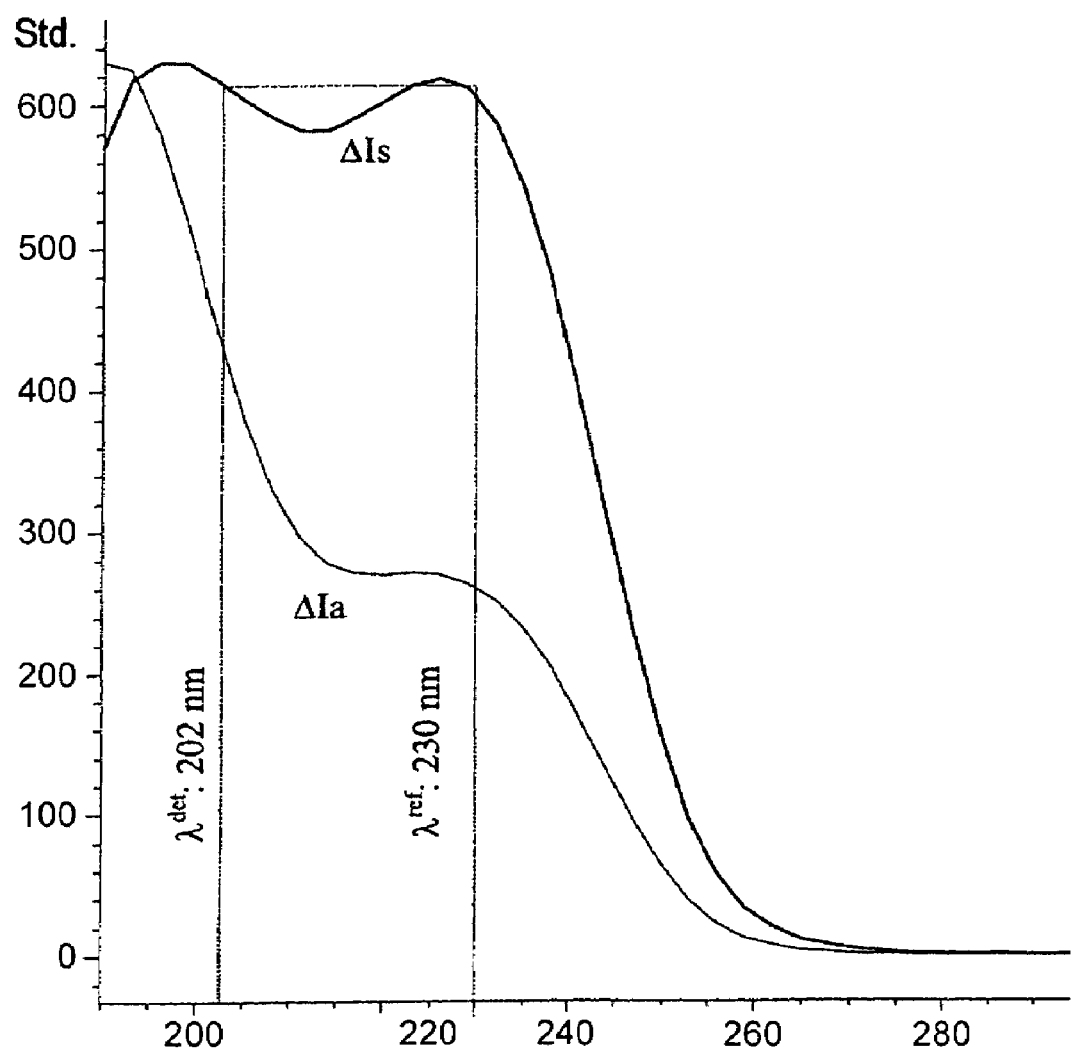
FIG. 1 illustrates the selective detection of acetylated oligosaccharides in which the UV spectrum of a sulfated disaccharide ΔIs is compared with that of an acetylated disaccharide ΔIa. The x-axis shows time in minutes and the y-axis shows the milliampere signal from the UV detector.

The examples below are intended to illustrate various features of the invention; however, the invention is not limited to the embodiments exemplified below.

Structural Symbols

| | | |
|---|---|---|
| ΔIVa = ΔU-GlcNAc | -IVa$_{id}$- = -IdoA-GlcNac- | -IVa$_{glu}$- = -GlcA-GlcNac- |
| ΔIVs = ΔU-GlcNS | ΔIVs$^{epi}$ = ΔGlcA-ManNS | -IVs$_{glu}$- = -GlcA-GlcNS— |
| ΔIVs = ΔU-GlcNS,3S | | -IVs$_{glu}$- = -GlcA-GlcNS— |
| ΔIIa = ΔU-GlcNac,6S | -IIa$_{id}$- = -IdoA-GlcNac,6S— | |

-continued

ΔIIIa = ΔU2S-GlcNAc -IIIa$_{id}$- = -IdoA2S-GlcNac-
ΔIIs$_{gal}$ = ΔGalA-GlcNS,6S -IIs$_{gal}$- = -GalA-GlcNS,6S—
ΔIIs = ΔU-GlcNS,6S -IIs$_{glu}$- = -GlcA-GlcNS,6S—
ΔIIs$^{epi}$ = ΔU-ManNS,6S IIs$_{glu}^{epi}$- = -GlcA-ManNS,6S—
ΔIIs = ΔU-GlcNS,3S,6S -IIs$_{glu}$- = -GcA-GlcNS,3S,6S—
ΔIIIs = ΔU2S-GlcNS -IIIs$_{id}$- = -IdoA2S-GlcNS—
ΔIIIs$^{epi}$ = ΔU2S-ManNS -IIIs$_{id}^{epi}$- = -IdoA2S-ManNS—
ΔIa = ΔU2S-GlcNac,6S -Ia$_{id}$- = -IdoA2S-GlcNac,6S—
ΔIs = ΔU2S-GlcNS,6S -Is$_{id}$- = -IdoA2S-GlcNS,6S—
ΔIs$^{epi}$ = ΔU2S-ManNS,6S -Is$_{id}^{epi}$- = -IdoA2S-ManNS,6S—
ΔIs = ΔU2S-GlcNS,3S,6S -Is$_{id}$- = -IdoA2S-GlcNS,3S,6S—

Materials: Methane sulfonic acid (99.5%) was purchased from Aldrich. All enzyme lyases from *Flavobacterium heparinum* (Heparinase I (EC 4.2.2.7), Heparinase II (no EC number), Heparinase III (EC 4.2.2.8)) were obtained from Grampian Enzymes (Aberdeen). Cetyl trimethyl ammonium hydrogensulfate was purchased from Merck (Darmstadt). All other reagents and chemicals were of the highest quality available. Water was purified with a Millipore purification system.

Example 1

Enzymatic Digestion

The following general method was used where appropriate in Examples 3 to 5.

Exhaustive digestion of heparin or oligosaccharides (0.1 mg) can be performed at room temperature for 48 h with a mixture of 10 mIU of heparinase I, 10 mIU of heparinase II, and 10 mIU of heparinase III in a total volume of 30 µl of 100 mM sodium acetate buffer, pH 7.0, containing 2 mM Ca(OAc)$_2$ and 2 mg/ml BSA. Partial digestion of heparin or oligosaccharides (0.1 mg) with heparinase I can be performed with 0.1 to 10 mIU of heparinase I in a total volume varying from 1 to 30 µl of 5 mM NaH$_2$PO$_4$, pH 7.0, containing 200 mM NaCl and 2 mg/ml BSA at 17° C. for 1 h to 10 days.

Example 2

CTA-SAX Chromatography

The following general methods were used where appropriate in Examples 3 to 5.

Apparatus: The chromatographic system used is a conventional Agilent 1100 system equipped with a UV diode array detector.

Dynamic column coating: The procedure used is similar to one described by Ito and Sunhara (Anal. Chem., 63 (1991) 273-276). A C$_8$ or C$_{18}$ reversed phase column filled with Hypersil BDS (From Thermo Finnigan) are used (150×2.1 mm I.D., particle size 3 µm). The columns are equilibrated for 240 min with 1 mM cetyl trimethyl ammonium hydrogensulfate in a H$_2$O—CH$_3$OH (68-32) v/v solution at a column temperature of 45° C. The amount of CTA adsorbed on the column is directly related to the methanol percentage contained in the percolated solution and can be modulated accordingly.

Chromatographic conditions: The column used are dynamically coated with CTA as already described. The developing ion is ammonium methane sulfonate prepared by neutralization to pH 2.5 of methane sulfonic acid by ammoniac aqueous solutions. The solvent B of CTA-SAX is 2 M ammonium methane sulfonate at pH 2.5. The solvent A is Milli-Q quality water adjusted to pH 3 by adding methane sulfonic acid. A linear gradient starting from 1% B to 100% B within 74 min is used at a flow rate of 0.22 ml.min$^{-1}$. After each run, a reconditioning step of 18 min is used. The column temperature is 40° C.

Using these conditions, volumes ranging between about 1 µl and about 1 ml can be injected depending on the concentration of oligosaccharides, the ionic strength of the sample, and the eluting power of the ion that can be achieved without peak broadening. For example, when fractions from analytical GPC are used (100 mM ammonium acetate), volumes up to 500 µl can be injected. Thus, when samples are contained in concentrated NaCl solutions (≈2 N), a 4- or 5-fold dilution in water is necessary before injection. In any case, injection of 400 µl of a NaCl solution diluted 4 times into water results in a better separation than is achieved when 100 µl of the initial NaCl solution is injected.

Figure 2:
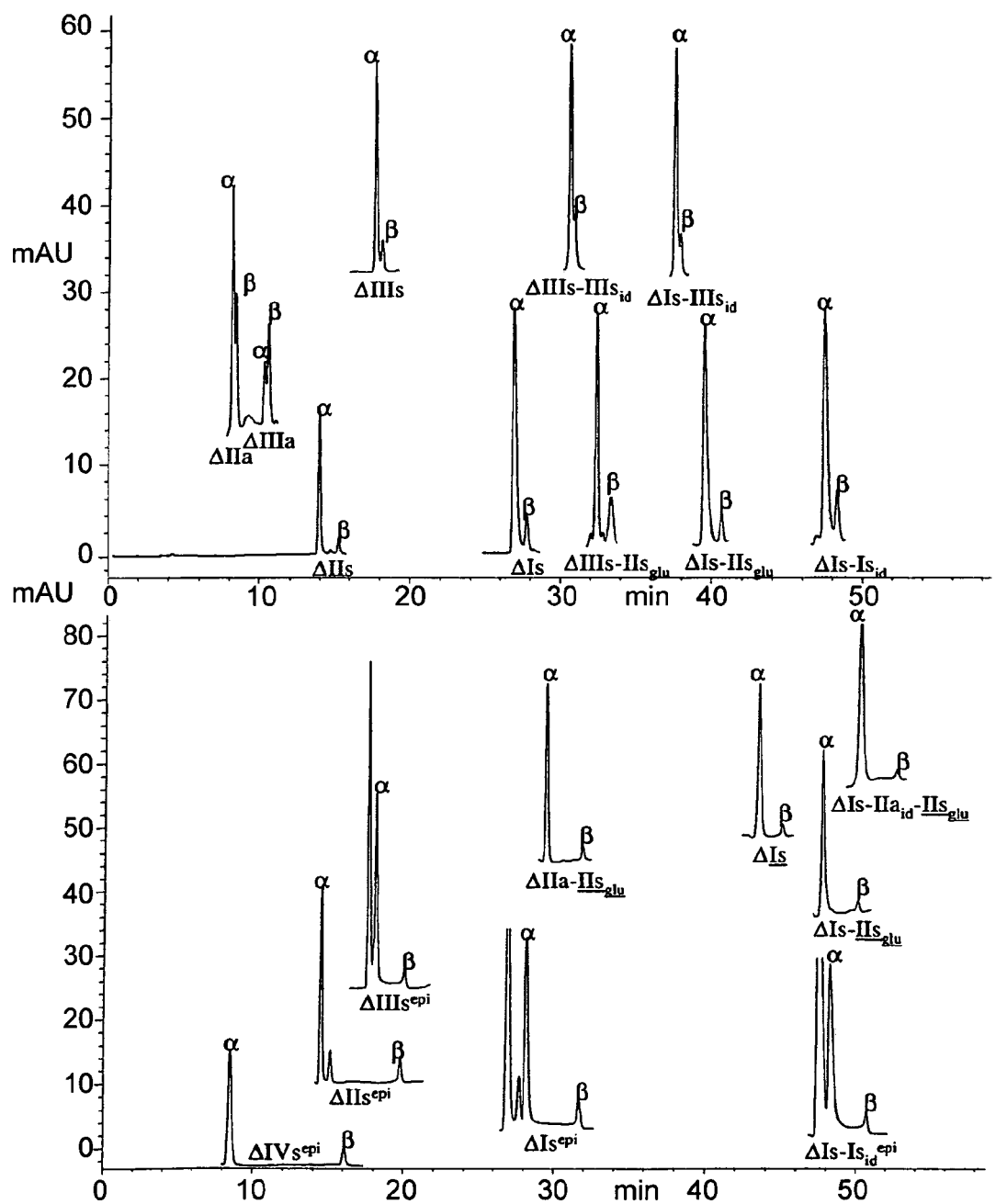
FIG. 2 shows the separation of oligosaccharide anomers on a CTA-SAX column. The x-axis shows time in minutes and the y-axis shows the milliampere signal from the UV detector.

The UV transparency of methane sulfonate permits the selective detection of functional groups using a diode array detector. Unsaturated oligosaccharides obtained by chemical or enzymatic β-elimination have characteristic UV spectra. The abbreviations used to symbolize the structure of the oligosaccharides are provided above. The UV spectra are mainly dependent on the pH of the mobile phase and on the presence of an N-acetyl group on the glucosamines. In a mobile phase at pH 2.5, it is possible to eliminate from the UV spectrum the contribution of non N-acetylated oligosaccharides by subtracting the absorbance at 247 nm (the reference wavelength) from that at 202 nm (the detection wavelength) (Huber, Diode array detection in HPLC, Chromatogr. Sci. Ser., 62 (1993) 363-392) as illustrated in FIG. 2. In the resulting signal, only N-acetylated oligosaccharides are detected. It will be understood that, for heparinic oligosaccharides, the UV spectrum depends on the pH of the mobile phase. As a consequence, if the pH is 6.0 instead of 2.5, the reference wavelength will be 230 nm instead of 247 nm. In all the chromatograms, two detection signals are given: a UV signal at 232 nm, which detects all unsaturated oligosaccharides and a signal corresponding to the difference in absorption at 202-247 nm, which specifically detects N-acetylated oligosaccharides. In a similar manner, baseline drift due to the elution gradient is subtracted with a blank run.

The CTA-SAX method may be used at a semi-preparative scale, using 250×21 mm columns filled with Hypersil BDS C$_{18}$ having a particle size of 5 µm. Column coating with CTA is done as for the analytical columns, with the column temperature adjusted to 45° C. Mobile phases are aqueous solutions with NaCl concentrations varying between 0 and 2.5 N. The pH is usually adjusted to 2.5 by adding diluted hydrochloric acid. Separations are achieved at room temperature using flow rates ranging between about 10 and about 20 ml.min$^{-1}$. UV detection at 234 nm is used. Collected fractions are neutralized by acetic acid and desalted on a GPC column as described below.

Analytical GPC: Analytical gel permeation is performed with 2 columns of TSK Super SW2000 (300×4.6 mm) with one guard TSK Super SW pre-column (35×4.6 mm) (TOSOH BIOSEP). Unsaturated oligosaccharides are detected by measuring UV adsorption at 232 nm. The mobile phase is 0.1M ammonium acetate, and the flow rate is 0.15 ml.min$^{-1}$. The injection volume is 5 μl. When GPC is coupled with CTA-SAX chromatography, the sample concentration must be high enough to allow detection in the next step. When a depolymerised sample is analyzed, its concentration in the GPC injected solution will vary depending on the sample, but may be between about 25 and about 100 mg/ml. The peaks corresponding to di, tetra, hexa, octa and decasaccharide are collected. Up to 250 μl of each fraction can be directly re-injected into the CTA-SAX column.

Desalting procedure: Oligosaccharides to be desalted are passed through columns filled with Sephadex® G-10 Superfine (Pharmacia) using water as the eluent. The column size may be chosen according to the quantity of sample to be desalted. A set of columns 100×7 cm, 100×5 cm, 40×2.6 cm, 20×1.6 cm are convenient for this purpose. Double detection by measuring conductivity and UV absorbance at 232 nm is performed.

Sequencing procedure: Purified oligosaccharides are collected after their separation on a 150×3 mm CTA-SAX column and desalted on a 20×1.6 cm Sephadex® G-10 column. Alternatively, the purified oligosaccharides may be simply diluted 5 times into water and neutralized to pH 7.0 by adding diluted NH$_3$. Sequencing is then performed by partial fragmentation using heparinases or 2-sulfatase. (R. Raman, et al., J. Biol. Chem. 278 (2003) 12167-12174; G. Venkataraman, et al., Science 286 (1999) 537-542; S. Ernst, et al., Critical Review in Biochemistry and Molecular Biology, (1995) 387-444).

In some analyses, a preliminary reduction of the oligosaccharides by NaBH$_4$ in 100 mM sodium acetate is achieved in order to mark the disaccharide positioned at the reducing end of the oligosaccharide chain. The fragmentation is monitored by HPLC injection on a 150×2.1 mm CTA-SAX column.

NMR Spectra: The samples were dissolved in 700 μl of 99% D$_2$O. One dimensional (1D) and 2 dimensional (2D) NMR spectra (COSY, TOCSY, ROESY, and HSQC) of the oligosaccharides were recorded at room temperature at 400.13 MHz, on a Bruker DRX400 spectrometer, using standard pulse sequences. The 2D homonuclear Hartmann-Hahn (TOCSY) experiments were recorded with a spin-lock time of 100 ms. The 2D ROESY spectrum was performed with mixing time of 400 ms. Chemical shifts are given in ppm with reference to external standard TSPD4. Proton chemical shifts were measured from the TOCSY experiment. Proton coupling constants could be measured directly on 1D spectra, when spectrum resolution was sufficient, and when proton signals did not overlap. Carbon chemical shifts were obtained from HSQC spectra. The structure determination was achieved using 1H and 13C NMR spectroscopy, together with TOCSY, ROESY and HSQC $^1$H/$^{13}$C 2D spectra.

Example 3

Exhaustive Depolymerization of Intestinal Porcine Heparin

Figure 3:
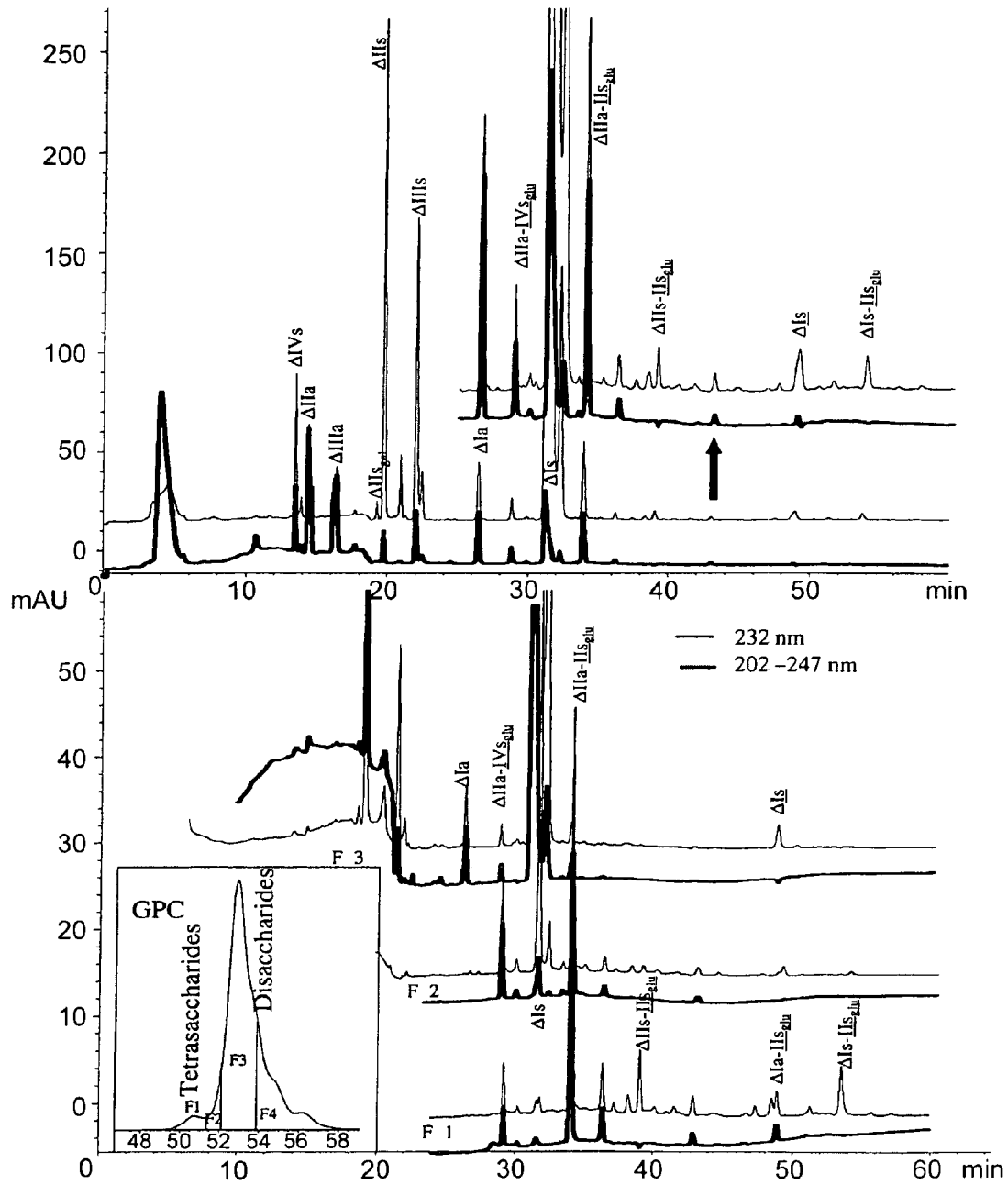
FIG. 3 illustrates the use of GPC/CTA-SAX coupling separate the oligosaccharides in a mixture obtained by the exhaustive depolymerization of intestinal porcine heparin. The x-axis shows time in minutes and the y-axis shows the milliampere signal from the UV detector.

FIG. 3 shows a CTA-SAX chromatogram of intestinal porcine heparin exhaustively depolymerised by the heparinase mixture described above and illustrates the benefit of the double detection method of the invention with coupled GPC and CTA-SAX columns. All of the elementary disaccharides were resolved with the exception of ΔIVa, which was not retained due to the absence of a sulfate function. Acetylated disaccharides ΔIIa, ΔIIIa and ΔIa were detected on both UV signals while N-sulfated disaccharides were only detected on the first signal (UV absorbance at 232 nm). The ability of the inventive methods to detect 3-O sulfated oligosaccharides is of note because these oligosaccharides are part of the ATIII binding sequence.

Not all of the oligosaccharides present in exhaustively depolymerised samples were resolved due to the heterogeneity of the disaccharide fraction, which comprises 5 different sulfation degrees (401<Mw<867). For tetrasaccharides, the weight average molecular weight range is between 1066 and 1330. For example, the two main tetrasaccharides (S. Yamada, et al., J. Biol. Chem., 270 (1995) 8696-8705) ΔIIa-IIs$_{glu}$ and ΔIIa-IVs$_{glu}$ (Mw 1066 and 1168) have molecular weights very close to the highly sulfated disaccharides. Therefore, only GPC fractions F1 to F3 were injected onto the CTA-SAX column. Low-sulfated disaccharide fraction F4 was of minor interest, and the ammonium acetate of the GPC mobile phase injected disturbed the beginning of the CTA-SAX chromatogram, corresponding to their elution range.

Subsequent to the separation, a new tetrasulfated disaccharide was identified in the heparin digest. A molecular weight of 767 Daltons was confirmed by LC/MS (unpublished results), which corresponds to a ΔIs structure. This disaccharide has been recently formed in vitro in heparin by the expression of 3-OST-5H. (Mochizuki, et al., J. Biol. Chem., 278 (2003) 26780-26787). This type of 3-O sulfated disaccharides is more abundant in exhaustively depolymerised heparin from intestinal bovine heparin. However, in samples of intestinal bovine heparin, the double UV detection method of the invention permits the detection of 2 similar disaccharides, ΔIIs and ΔIIIs, and also the 3-O sulfated tetrasaccharides ΔIIs-IIs$_{glu}$, ΔIs-IIs$_{glu}$, and ΔIa-IIs$_{glu}$. The presence of a 2-O sulfate function on the unsaturated acid shifts the maximum absorption wavelength, allowing their recognition. Treatment of heparinase resistant tetrasaccharides with a large excess of the heparinase mixture allowed partial depolymerization and characterization of the disaccharide products. For example, under those conditions, ΔIa-IIs$_{glu}$ was partially transformed into ΔIa and ΔIIs.

Example 4

Depolymerization of Intestinal Porcine Heparin by Heparinase 1

Depolymerization of intestinal porcine heparin by heparinase 1 has been studied and many of the resulting oligosaccharides have been identified. The highly evolutive character of this mixture, due to the continuous advancement of the cleavage by heparinase 1, has been demonstrated. A mixture of disaccharides, tetrasaccharides, and hexasaccharides is generally recovered at the end of the reaction mainly due to the resistance of acetylated sites -Glc(NS, 6-OH or 6S)↓IdoA (2-OHor 2S)-GlcNAc(6-OH or 6S)↓GlcA- to heparinase 1, which generates hexasaccharides and the resistance of -GlcNS(6-OHor 6S)↓GlcA-, which generates tetrasaccharides.

Figure 5:
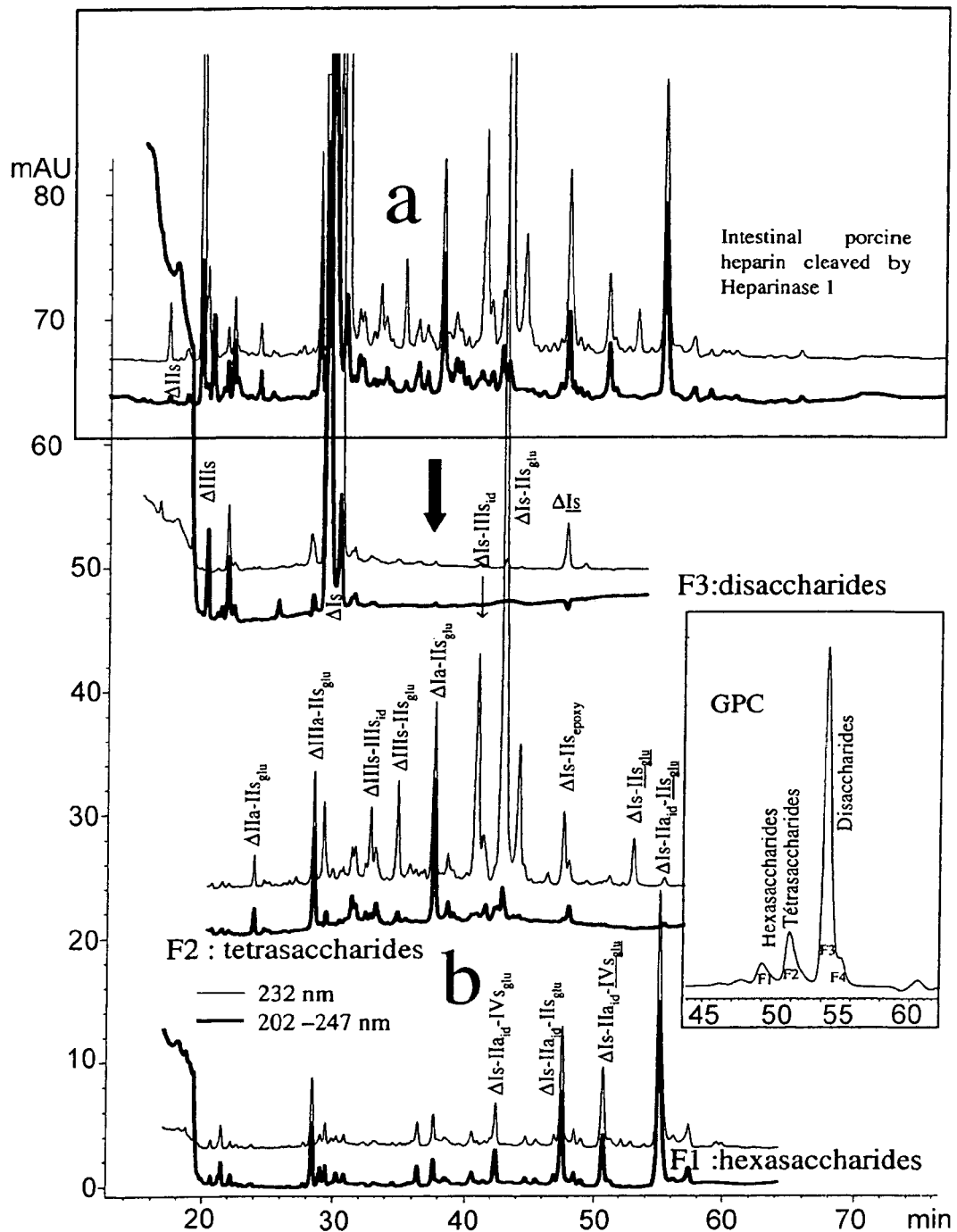
FIGS. 5a and 5b illustrates the use of GPC/CTA-SAX coupling to separate the oligosaccharides in a mixture obtained by the complete heparinase 1 depolymerization of intestinal porcine heparin. The x-axis shows time in minutes and the y-axis shows the milliampere signal from the UV detector.

FIG. 5a shows a complete chromatogram of intestinal porcine heparin digested by heparinase 1 with related chromatograms of its disaccharide, tetrasaccharide and hexasaccharide fractions (FIG. 5b). The complete transformation of the ΔIs- Is$_{id}$ tetrasaccharide into the ΔIs disaccharide showed that the enzymatic reaction was almost complete. The illustrated separation could not be achieved using CTA-SAX chromatography alone because certain low sulfated hexasaccharides were eluted in the same time range as certain sulfated tetrasaccharides. The chromatogram of the disaccharidic fraction contained ΔIs, ΔIIs, ΔIIIs as well as 3-O sulfated ΔIs. Tetrasaccharidic fraction contained ΔIs-IIIs$_{id}$, ΔIs-IIs$_{glu}$, ΔIIIs-IIIs$_{id}$ and ΔIIIs-IIs$_{glu}$, in agreement to reported structures isolated in many articles. See, e.g., H. Mochizuki, et al., J. Biol. Chem. 278 (2003) 26780-26787.

In the present invention, structural recognition was achieved by the action of heparinase 2 on the isolated heparinase 1-resistant tetrasaccharides, leading after cleavage to a mixture of disaccharide building blocks. In the case of ΔIs-IIs$_{glu}$ and ΔIIIs-IIs$_{glu}$, the possible ΔIIs-Is$_{id}$ and ΔIIs-IIIs$_{id}$ sequences were eliminated considering the maximum of UV absorption and the anomeric elution pattern. Application of Lindahl's rules (J. Biol. Chem. 265 (1990) 7292-7300) eliminated the second possibilities ΔIs-IIs$_{id}$ and ΔIIIs-IIs$_{id}$ since the iduronic configuration of IIs (i.e., GlcA-GlcNS) hardly ever exists in heparin. The most difficult case was the distinction between ΔIs-IIIs$_{id}$ and ΔIs-Is$_{id}$. This was done by a preliminary reduction by NaBH$_4$ of the predicted tetrasaccharide ΔIs-IIIs$_{id}$. The action of a large excess of a mixture of heparinases 1, 2, and 3 on a well-desalted sample could cleave the reduced tetrasaccharide, affording ΔIs with the reduced ΔIIIs (easily identified by the absence of anomer) disaccharides. ΔIs-IIs$_{glu}$ was also present, as in the exhaustively depolymerised sample. A new structure (ΔIs-IIs$_{epoxy}$) was also identified in this mixture:

Integration of the signals of the 1D proton spectrum (FIG. 4) together with the analysis of the TOCSY spectrum, indicate that the compound has the properties of a tetrasaccharide. A weak signal observed at 3.01 ppm indicates the presence of the other alpha anomer residue (15%) at the reducing end. The ethylenic proton H4 observed at 5.95 ppm is used to start assignment of the 4,5-unsaturated uronic acid. And four anomeric protons corresponding to four residues are clearly identified on TOCSY spectrum. Interproton coupling constants are in full agreement with data published (Abdel-Malik, et al., Carbohydr. Res., 159 (1987) 11-23). Evidence of the β-(1->4)- O-glucosidic bond are observed on ROESY spectrum from inter residue correlations. Protons and carbon chemical shifts, together with 2D spectra observed correlations, are compatible with ΔIs-IIs$_{epoxy}$.

This tetrasaccharide, ΔIs-IIs$_{epoxy}$, which is generated by 2-O desulfation of ΔIs-(Is$_{id}$)$_n$ (R. N. Rej, et al., Carbohydr. Res., 200 (1990) 437-447; M. Jaseja, et al., Can. J. Chem., 67 (1989) 1449-1456; S. Piani, et al., J. Carbohydr. Chem. 12 (1993) 507-21; U. R. Desai, et al., Carbohydr. Res., 241 (1993) 249-259), was isolated from bovine lung heparin treated with alkaline conditions (NaOH 1N) for 30 min at 60° C. Heparinase 1 depolymerization allowed isolation and characterization of the component by NMR. This intermediate is relatively unstable and undergoes further hydrolysis into either L-iduronic or L-galacturonic moieties (M. Jaseja, et al., Can. J. Chem., 67 (1989) 1449-1456; U. R. Desai, et al., Carbohydr. Res., 241 (1993) 249-259).

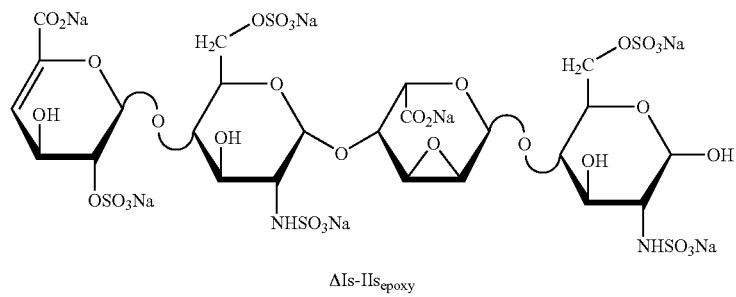

ΔIs-IIs$_{epoxy}$

The structure was determined using 1H and 13C NMR spectroscopy, together with COSY, TOCSY, ROESY and HSQC $^1$H/$^{13}$C 2D spectra. The full $^1$H and $^{13}$C assignments are reported hereafter (Proton and carbon chemical shifts of ΔIs-IIs$_{epoxy}$):

The N-Acetylated tetrasaccharides ΔIa-IIs$_{glu}$, ΔIIIa-IIs$_{glu}$ and ΔIIa-IIs$_{glu}$ were also identified. They appeared in the last part of the depolymerization as a result of the cleavage of the N-acetylated hexasaccharides according to the following scheme:

| ΔIs-IIs$_{epoxy}$: ΔU 2S-GlcNS,6S-GulA 2,3epo-GlcNS,6S | | | |
|---|---|---|---|
| ΔU 2S | GlcNS,6S | GulA 2,3epo | GlcNS,6S |
| 1 5.46 (3.0)/97.8 | 5.40 (3.5)/95.2 | 5.40 (3.5)/96.5 | 5.42 (3.5)/91.8 |
| 2 4.59 (1.0)/75.1 | 3.28 (10.5; 3.5)/58.0 | 3.70 (3.5)/52.0 | 3.23 (10.5; 3.5)/58.5 |
| 3 4.29/63.2 | 3.58 (10.5; 9.0)/70.0 | 3.79 (3.0)/51.2 | 3.60 (10.5; 9.0)/70.1 |
| 4 5.95 (5.0; 1.0)/106.7 | 3.81 (10.0)/78.5 | 4.46 (1.0)/70.2 | 3.81 (10.0)/78.5 |
| 5 —/nm [1] | 4.10 (10.0)/64.2 | 4.31/69.0 | 3.92 (9.5; 2.0)/64.0 |
| 6 —/nm | 4.32 – 4.18 (10.5)/66.7 | —/nm | 4.32 (10.5; 2.0) – 4.21/67.2 |

[1] nm: not measured

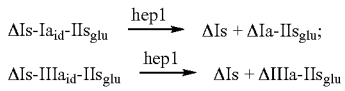

2-O sulfatation of the iduronic acid favored cleavage at the site -Glc(NS,6S)↓IdoA(2S)-GlcNAc(6-OH or 6S). The presence of ΔIIa-IIs$_{glu}$ showed that the reaction

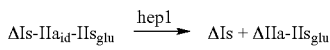

is possible, but was incomplete. In the hexasaccharidic fraction, the absence of ΔIs-Ia$_{id}$-IIs$_{glu}$ and ΔIs-IIIa$_{id}$-IIs$_{glu}$ showed that they were completely cleaved. On the other hand, ΔIs-IIa$_{id}$-IIs$_{glu}$ was still present as a major constituent of the hexasaccharidic fraction. Other constituents of the hexasaccharidic fraction, ΔIs-IIa$_{id}$-IIs$_{glu}$, ΔIs-IIa$_{id}$-IVs$_{glu}$ and ΔIs-IIa$_{id}$-IVs$_{glu}$, were first identified using our sequencing techniques and then isolated by preparative chromatography and their identity was confirmed by NMR spectroscopy. 3-O sulfated hexasaccharides were identified by the action of heparinase 2 using reactions such as:

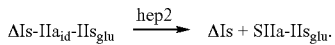

Considering this fragmentation scheme, the possible presence of a ΔIIa-IIs$_{glu}$-Is$_{id}$ structure was eliminated by examining both the UV spectrum and the anomeric pattern. The 2 other hexasaccharides, ΔIs-IIa$_{id}$-IIs$_{glu}$ and, ΔIs-IIa$_{id}$-IVs$_{glu}$ were identified in a similar way using the action of heparinase 1, heparinase 3+heparinase 1, and then the mixture of the 3 heparinases.

As already mentioned, the action of heparinase 1 1 can lead to ΔIIa-IIs$_{glu}$ and ΔIIa-IVs$_{glu}$.

ΔIs-IIa$_{id}$-IIs$_{glu}$ $\xrightarrow{\text{hep3 + hep1}}$ ΔIs-IIa$_{id}$ + ΔIIs $\xrightarrow{\text{hep3 + hep1}}$ ΔIs + ΔIIa + ΔIIs.

Note that the transformation of ΔIs-IIa$_{id}$ into disaccharide building blocks was due to the action of heparinase 3. After identical enzymatic treatment, ΔIs-IIIa$_{id}$-IIs$_{glu}$ was only fragmented into ΔIs-IIIa$_{id}$+ΔIIs. Here, cleavage by heparinase 1 of ΔIs↓IIIa$_{id}$ is impossible in contrast with ΔIs↓IIIa$_{id}$-IIs$_{glu}$. Many oligosaccharides with an acetylated glucosamine in the reducing end such as ΔIs-IIa$_{id}$ or ΔIs-IIIa$_{id}$ have the specific anomeric pattern in CTA-SAX chromatography similar to ΔIIa or ΔIIIa. If desired, this is another way to identify oligosaccharides with N-acetylated moieties at the reducing end. To conclude with the transformation of acetylated hexasaccharides by heparinase 1 into tetrasaccharides, the following order by increasing cleavability has been established:
ΔIs-IIa$_{id}$-IIs$_{glu}$≈ΔIs-IIa$_{id}$-IVs$_{glu}$<ΔIs-IIa$_{id}$-IIs$_{glu}$≈ΔIs-IIa$_{id}$-IVs$_{glu}$<ΔIIs-IIIa$_{id}$-IIs$_{glu}$≈ΔIIIs-IIIa$_{id}$-IVs$_{glu}$<ΔIs-IIIa$_{id}$-IIs$_{glu}$≈ΔIs-IIIa$_{id}$-IVs$_{glu}$>ΔIs-Ia$_{id}$-IIs$_{glu}$.

Figure 4:
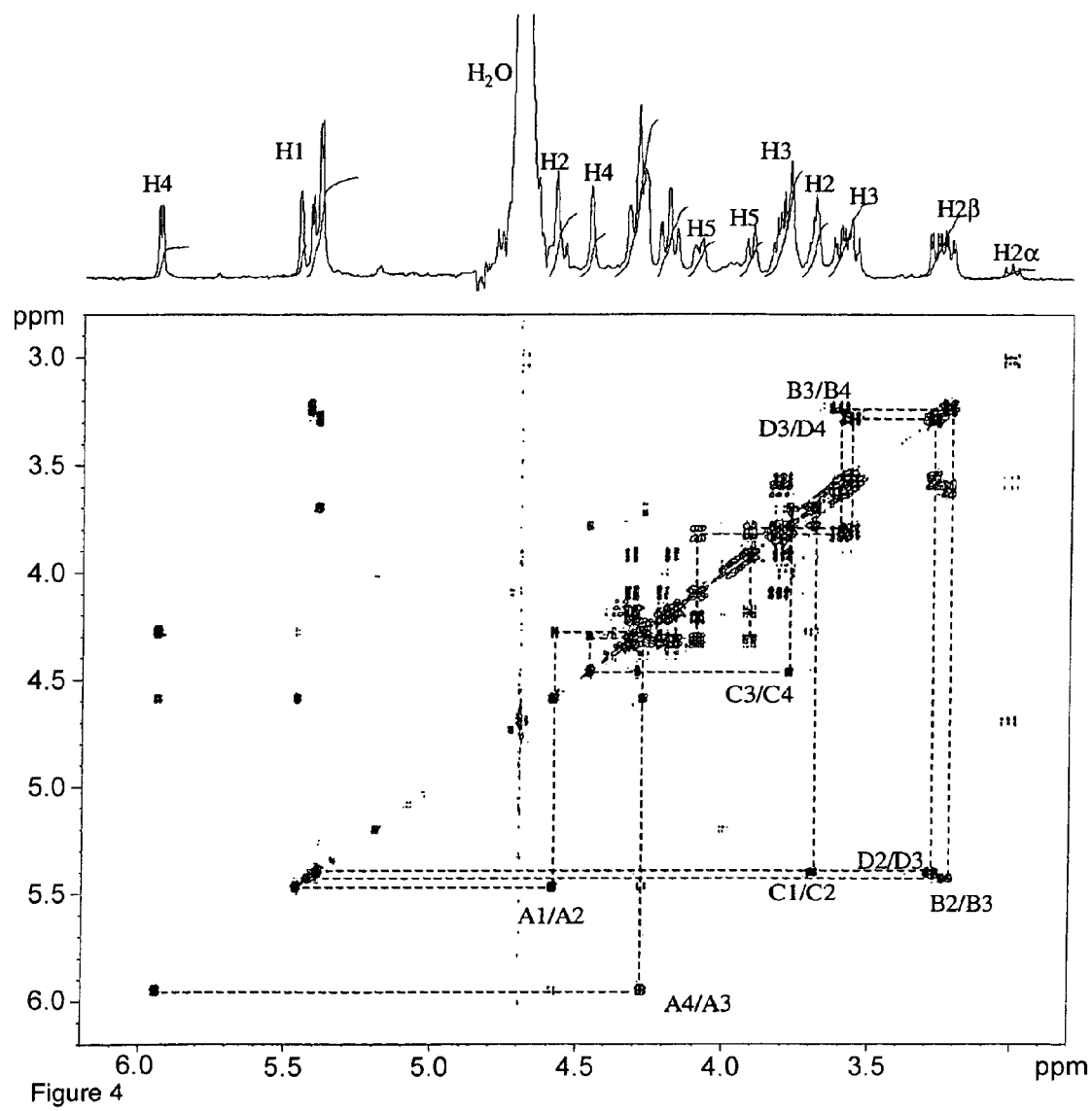
FIG. 4 illustrates the Proton and COSY spectra of ΔIs-IIs$_{epoxy}$ in $D_2O$-400 MHz. The main cross-peaks are labeled with the letter corresponding to the saccharide unit and proton number z.
Figure 6:
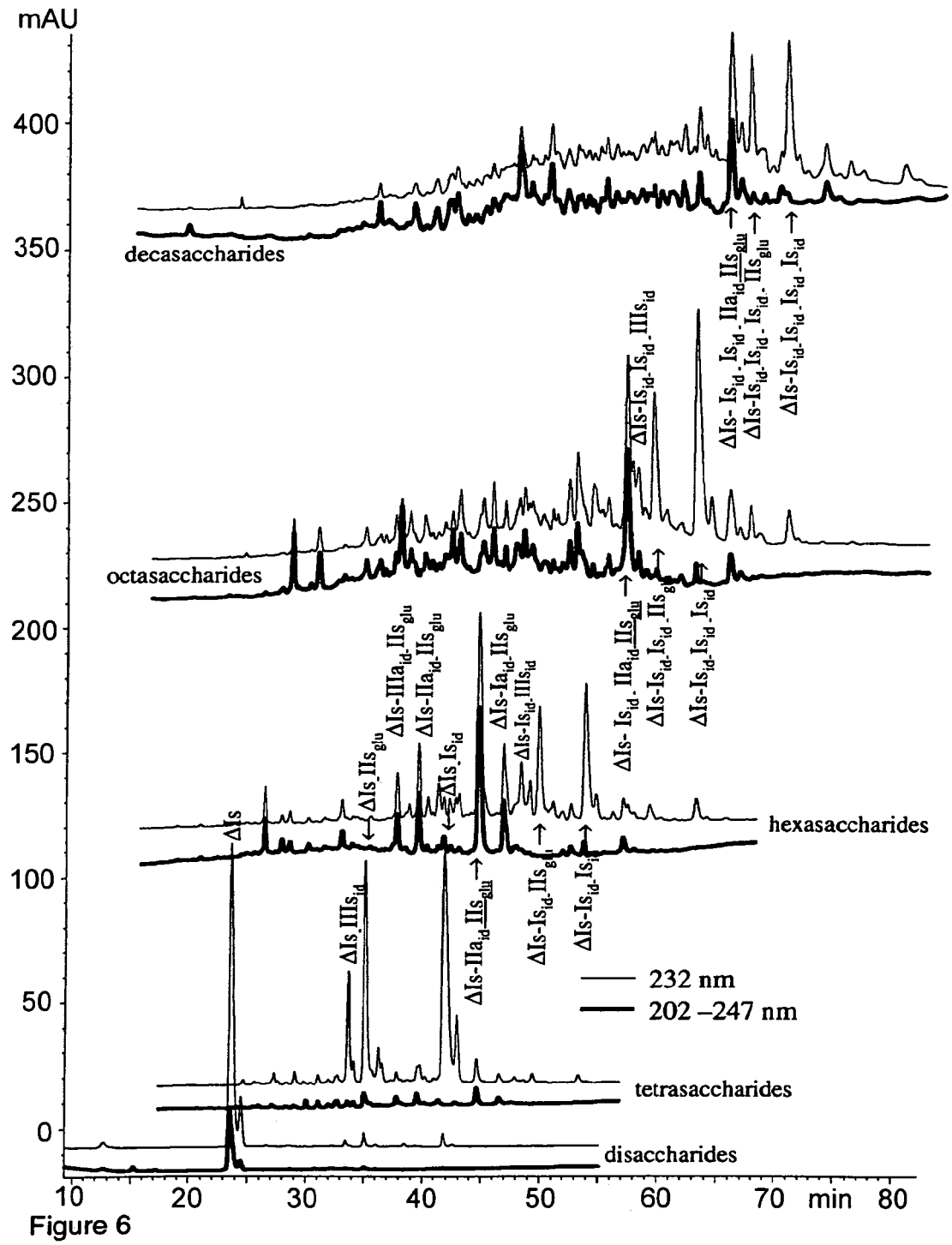
FIG. 6 illustrates the use of GPC/CTA-SAX coupling to separate the oligosaccharides in a mixture obtained by the partial depolymerization of intestinal porcine heparin by heparinase 1. The x-axis shows time in minutes and the y-axis shows the milliampere signal from the UV detector.

FIG. 6 shows CTA-SAX chromatograms of fractions from intestinal porcine heparin partially depolymerised by heparinase 1. This figure illustrates the high resolving power of CTA-SAX even with highly sulphated oligosaccharides. Comparing the contents of the tetrasaccharide and hexasaccharide fractions of FIG. 3 and FIG. 4 illustrates the influence of the progression of heparin cleavage by heparinase 1.

Example 5

Example of Sequencing

Figure 7:
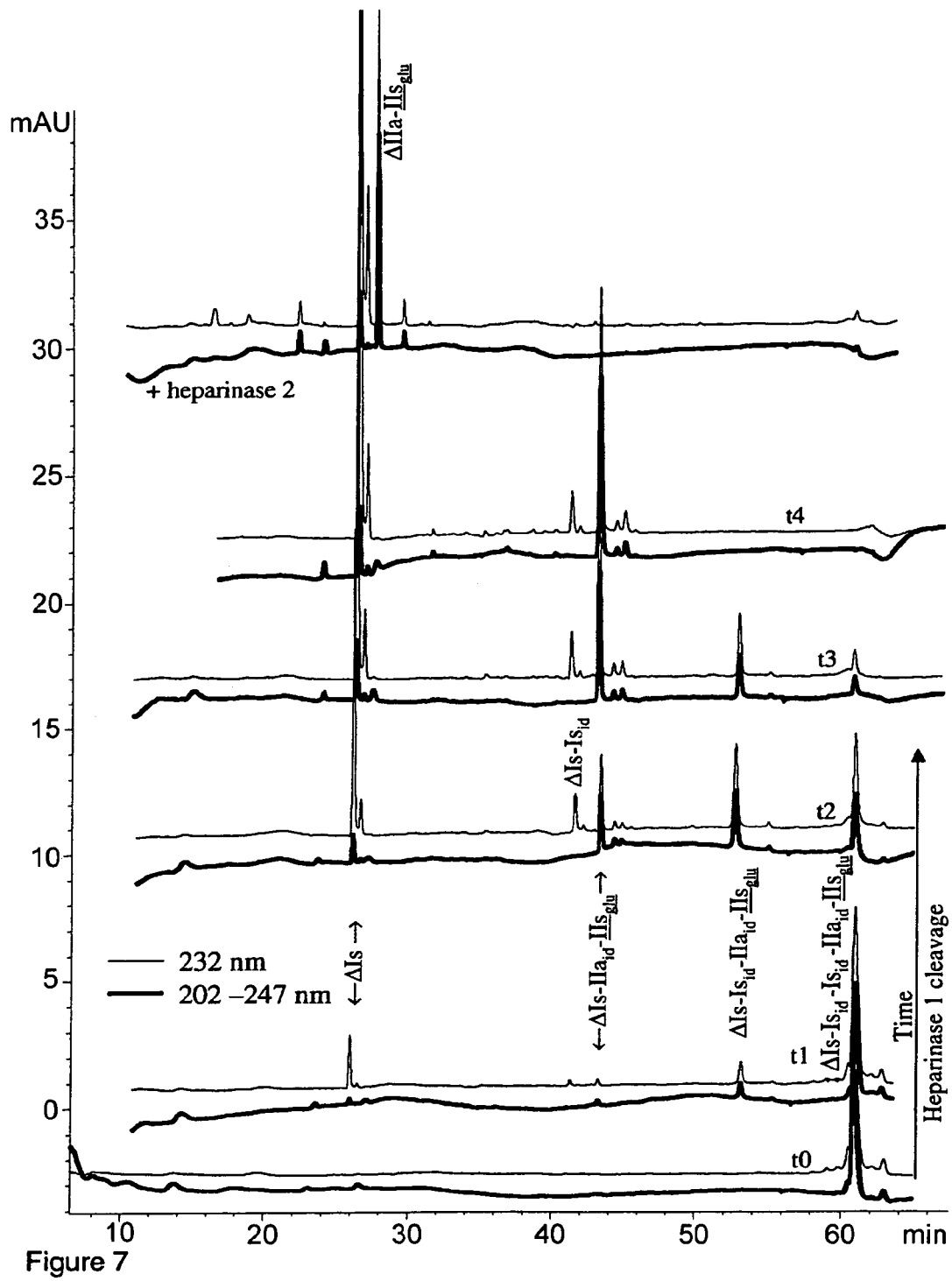
FIG. 7 illustrates the sequencing of ΔIs-Is$_{id}$-Is$_{id}$-IIa$_{id}$-IIs$_{glu}$. The x-axis shows time in minutes and the y-axis shows the milliampere signal from the UV detector.

A simplified technique for sequencing oligosaccharides has been developed, which is based on controlled depolymerization by heparinases. The resolving power of CTA-SAX combined with selective UV detection, made it possible to identify the fragmentation scheme and deduce the starting material structure. The weak point of methods based on analysis of digests with lyases such as heparinases is the relative uncertainty regarding the configuration of uronic acids due to their disappearance after the generation of the unsaturated bond during the cleavages (β-elimination) (Y. Kariya, et al, *J. Biochem.* 123(1998)240-246). This uncertainty is in fact rather small if the rules on heparin disaccharide configuration and linkage are taken into account. When necessary, the acid configurations were confirmed by NMR techniques. Our sequencing methodology improved with our knowledge of heparin oligosaccharide structures. It started with the identification of elementary tetrasaccharides, and continued progressively with hexasaccharides and higher oligosaccharides. FIG. 7 shows an example of sequencing of the ΔIs-Is$_{id}$-Is$_{id}$-IIa$_{id}$-IIs$_{glu}$ decasaccharide: When heparinase 1 was applied, two sites were cleaved: ΔIs↓Is$_{id}$↓Is$_{id}$-IIa$_{id}$-IIs$_{glu}$. A mixture of 4 fragments, ΔIs-Is$_{id}$-IIa$_{id}$-IIs$_{glu}$, ΔIs-IIa$_{id}$-IIs$_{glu}$, ΔIs-Is$_{id}$ and ΔIs was observed. With further progress of the reaction, ΔIs-Is$_{id}$-IIa$_{id}$-IIs$_{glu}$ was cleaved into ΔIs-IIa$_{id}$-IIs$_{glu}$ and ΔIs. The acetylated fragments were easily detected using dual wavelength UV detection. When heparinase 2 was applied, the three sites ΔIs↓Is$_{id}$↓Is$_{id}$↓IIa$_{id}$-IIs$_{glu}$ were cleaved. When these sites were cleaved, the remaining fragments were ΔIIa-IIs$_{glu}$ and ΔIs. Considering the structure of the identified fragments, the only structural possibility for the sequenced decasaccharide is ΔIs-Is$_{id}$-Is$_{id}$-IIa$_{id}$-IIs$_{glu}$. Sequencing ΔIs-Is$_{id}$-IIa$_{id}$-IIs$_{glu}$-Is$_{id}$ is not possible as it cannot give fragments of ΔIs-Is$_{id}$ by heparinase 1 cleavage. The other possibility, ΔIs-IIa$_{id}$-IIs$_{glu}$-Is$_{id}$-Is$_{id}$, was eliminated both by the recognition of its octasaccharide fragment ΔIs-Is$_{id}$-IIa$_{id}$-IIs$_{glu}$ and also by the anomeric pattern of the starting decasaccharide In a method for quantification according to the invention, the widely accepted hypothesis that all the unsaturated oligosaccharides contained in the mixture have the same molar absorptivity, equal to 5500 mol$^{-1}$.l.cm$^{-1}$ is made. It is therefore possible to determine the percentage by weight of all the constituents of the depolymerized mixture in the starting low-molecular-weight heparin.

What is claimed is:

1. A method of assaying a sample chosen from heparin, low-molecular-weight heparin, ultra low molecular weight heparin, and oligosaccharides, the method comprising
analyzing the sample using a reversed phase strong anion exchange column coated with at least one cetyl trimethylammonium salt (CTA-SAX)
wherein the analyzing comprises selectively detecting acetylated sugars by substracting an absorbance measured at a first wavelength at which both acetylated and non-acetylated sugars absorb from an absorbance measured at a second wavelength at which acetylated but not non-acetylated sugars absorb,
wherein the first and second wavelengths are different, and wherein the two absorbances are measured using a UV detector to simultaneously detect absorbance at the first and the second wavelengths.

2. The method according to claim 1, wherein the reversed phase column is a $C_8$ or $C_{18}$ column.

3. The method according to claim 1, wherein all of the oligosaccharides from disaccharides to dodecasaccharides are detected.

4. The method according to claim 2, wherein the sample is fractionated by Gel Permeation Chromatography (GPC) prior to the chromatographic separation using the $C_8$ or $C_{18}$ reversed phase column.

5. The method according to claim 2, wherein the sample is depolymerized either partially or totally prior to the chromatographic separation using the $C_8$ or $C_{18}$ reversed phase column.

6. The method according to claim 2, wherein the sample is reduced after it is depolymerised and prior to the chromatographic separation using the $C_8$ or $C_{18}$ reversed phase column.

7. The method of claim 1, wherein:
prior to analyzing the sample using a reversed phase strong anion exchange column coated with at least one cetyl trimethylammonium salt (CTA-SAX) the sample is processed by a method comprising
 (a) depolymerizing the sample by enzymatic depolymerization
 (b) reducing the depolymerized sample; and
 (c) assaying the sample of step (a) and/or step (b) by CTA-SAX chromatography.

8. The method according to claim 7, wherein the sample is enzymatically depolymerised using at least one heparinase.

9. The method according to claim 8, wherein the at least one heparinase is chosen from heparinase 1 (EC 4.2.2.7.), heparinase 2 (heparin lyase II), and heparinase 3 (EC 4.2.2.8.).

10. The method according to claim 8, wherein the sample is enzymatically depolymerised using a mixture of heparinases comprising heparinase 1 (EC 4.2.2.7.), heparinase 2 (heparin lyase II), and heparinase 3 (EC 4.2.2.8.).

11. The method according to claim 6, wherein the sample is reduced by $NaBH_4$ or by an alkali metal salt of the borohydride anion.

12. The method according to claim 1, wherein the low-molecular weight heparin is enoxaparin sodium.

13. The method according to claim 6, wherein the sample is enoxaparin sodium and the sample is reduced to reduce the reducing ends of said enoxaparin sodium which are not in the 1,6-anhydro form.

14. The method according to claim 1, wherein the chromatographic separation uses a mobile phase which is transparent to UV light having wavelengths in the range of about 200 nm to about 400 nm.

15. The method according to claim 1, wherein the chromatographic separation uses a mobile phase comprising methane sulfonate salts.

16. The method according to claim 1, wherein the chromatographic separation uses a mobile phase comprising ammonium methane sulfonate or sodium methane sulfonate.

17. The method according to claim 2, wherein chromatography on the $C_8$ or $C_{18}$ reversed phase column is performed at a pH of from about 2.0 to about 7.0.

18. The method according to claim 2, wherein chromatography on the $C_8$ or $C_{18}$ reversed phase column is performed at a pH of from about 2.5 to about 3.0.

19. The method according to claim 2, wherein chromatography on the $C_8$ or $C_{18}$ reversed phase column coated with a quaternary ammonium salt is performed in a mobile phase comprising water adjusted to a pH of about 3 by adding methane sulfonic acid and/or 2 M ammonium methane sulfonate, a pH of about pH 2.5.

20. The method according to claim 1, further comprising detecting the presence of oligosaccharide chains whose end is modified with a 1,6-anhydro bond.

21. The method according to claim 1, wherein the acetylated sugars detected are at least one acetylated oligosaccharide chosen from ΔIVa, ΔIIa, ΔIIIa, ΔIa, ΔIIa-IVs$_{glu}$, and ΔIIa-IIs$_{glu}$.

22. The method according to claim 1, wherein the low-molecular weight heparin is any LMWH seeking approval by a regulatory authority pursuant to an application citing Lovenox®/Clexane® (enoxaparin sodium injection) as the listed drug.

23. The method of claim 1, wherein at least one saccharide chosen from any of the following four saccharides is detected

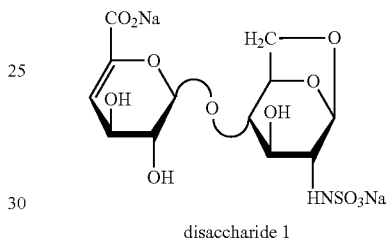
disaccharide 1

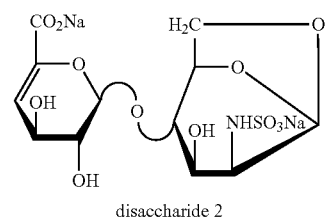
disaccharide 2

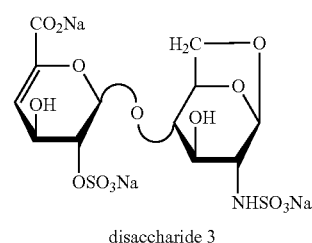
disaccharide 3

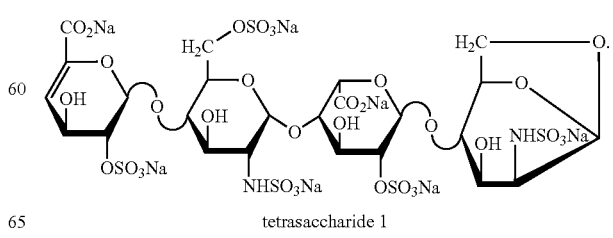
tetrasaccharide 1

24. The method of claim 1, wherein the following saccharide is detected
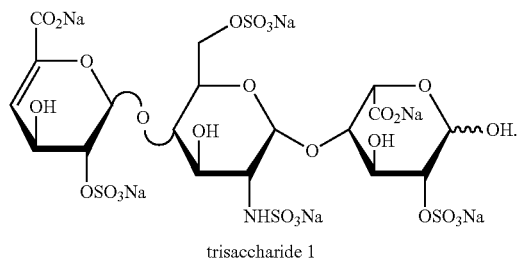
trisaccharide 1
25. The method of claim 1, wherein at least one saccharide chosen from any of the following saccharides is detected:
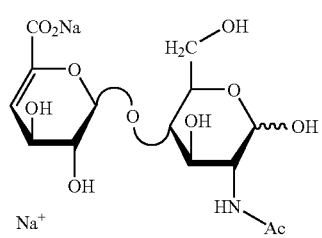
ΔIVa
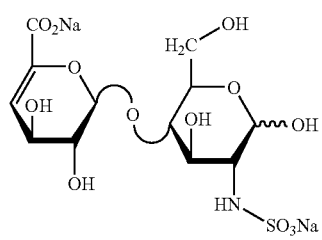
ΔIVs
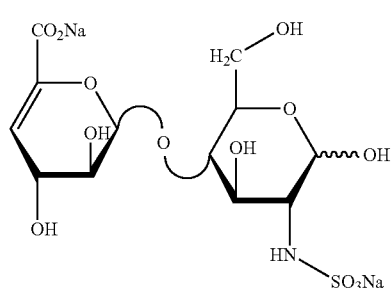
ΔIVs$_{gal}$
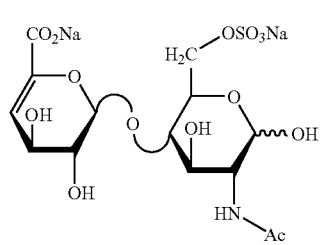
ΔIIa
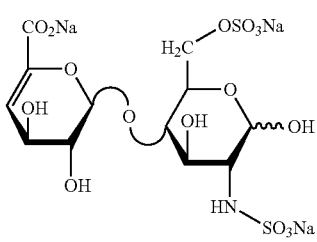
ΔIIs
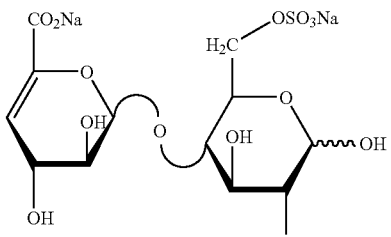
ΔIIs$_{gal}$
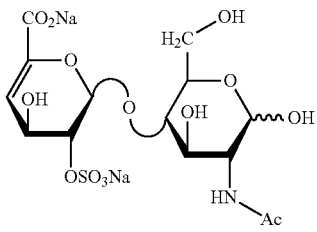
ΔIIIa
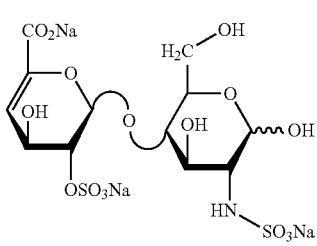
ΔIIIs
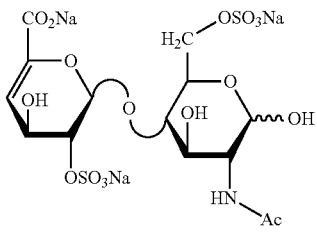
ΔIa
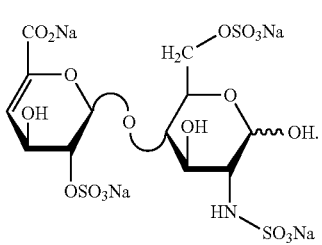
ΔIs
* * * * *